United States Patent [19]

Martin et al.

[11] Patent Number: 4,957,918

[45] Date of Patent: Sep. 18, 1990

[54] TOPICAL TREATMENT OF BLEPHARITIS

[75] Inventors: Neil F. Martin, Silver Spring; Howard N. Robinson, Lutherville, both of Md.

[73] Assignees: Leonard Bloom; Marvin S. Towsend, both of Towson, Md. ; a part interest

[21] Appl. No.: 204,547

[22] Filed: Jun. 9, 1988

[51] Int. Cl.$^5$ .................. A61K 31/415; A61K 31/535

[52] U.S. Cl. .................................. 514/235.8; 514/398; 514/914

[58] Field of Search ............................ 514/398, 235.8

[56] References Cited

U.S. PATENT DOCUMENTS 4,041,168 8/1977 Assandri et al. ..................... 514/398
4,491,588 1/1985 Rosenburg et al. ............ 514/398 X

OTHER PUBLICATIONS

Chemical Abstracts, 98:209546a (Mattila et al.), 1983.
"Ocular Rosacea" by M. S. Jenkins et al., American Journal Ophthalmology, vol. 88:618–622 (1979).
"Blepharitis Associated with Acne Rosacea and Seborrheic Dermatitis" by J. P. McCulley et al., Oculocutaneous Diseases, edited by J. P. Callen et al., Little, Brown, & Company, International Ophthalmology Clinics, Spring 1985, vol. 25, No. 1, pp. 159–172.
"Ocular Rosacea" by D. J. Browning et al., Survey of Ophthalmology, vol. 31, No. 3, Nov.–Dec. 1986, pp. 145–158.
Textbook of Dermatology, 4th Edition, A. Rook et al., editors, vol. 2, p. 2152.
"Topical Metronidazole Therapy for Rosacea" by P. A. Bleicher et al., Arch. Dermatol., vol. 123, May 1987, pp. 609–614.
Diseases of the Cornea, 2nd Edition, by M. G. Grayson, C. Z. Mosby Company, 1983, pp. 199–209.
"Tear Physiology and Dry Eyes" by F. J. Holly et al., Survey of Ophthalmology, vol. 22, No. 2, Sep.–Oct. 1977, pp. 69–87.

*Primary Examiner*—Leonard Schenkman
*Attorney, Agent, or Firm*—Leonard Bloom

[57] ABSTRACT

A method and composition for treating blepharitis or blepharoconjunctivitis comprises topical administration of a nitroimidazole compound, e.g. metronidazole in a suitable carrier directly to affected ocular tissues. The carrier can be an artificial tear solution or an ointment or water soluble gel base.

13 Claims, No Drawings

TOPICAL TREATMENT OF BLEPHARITIS

FIELD OF THE INVENTION

The present invention relates to the field of treating abnormal eye inflammation and more particularly to the topical treatment of inflammations and other dysfunctions of the eyelid and conjunctiva. The present invention is especially concerned with the treatment of blepharitis and blepharoconjunctivitis particularly associated with ocular rosacea.

Background Of The Invention

Blepharitis is an inflammation of the eyelids. Blepharoconjunctivitis is an inflammation of the eyelids and the conjunctiva of the eye. Both conditions are associated with the condition known as ocular rosacea.

Rosacea is a disease of the skin (acne rosacea) and eyes (ocular rosacea) of unknown etiology and a variety of manifestations. The clinical and pathological features of the eye disease are nonspecific, and the disease is widely underdiagnosed by ophthalmologists.

More specifically with respect to ocular rosacea, ocular rosacea may involve the eyelids, conjunctiva, and cornea. Common manifestations of ocular rosacea include blepharitis, blepharoconjunctivitis, meibomianitis, chalazia, styes and conjunctival hyperemia.

References which discuss ocular rosacea include: "Ocular Rosacea" by M. S. Jenkins et al, American Journal of Opthalmology, Vol. 88:618-622 (1979); "Blepharitis Associated With Acne Rosacea and Seborheic Dermatitis" by J. P. McCulley et al, in Oculocutaneous Diseases, edited by J. P. Callen et al, Little, Brown & Company, International Ophthalmology Clinics, Spring 1985, Vol, 25, No. 1, pp. 159-172; and "Ocular Rosacea" by D. J. Browning et al, Survey of Ophthalmology, Vol. 31, No. 3, November-December 1986, pp. 145-158.

In the article by McCulley et al mentioned above, on pages 170-172, several treatments for blepharitis are disclosed. These treatments include: topical antibiotics; oral tetracycline; SSA neutralizers; exoenzymatic inhibitors; vitamin A analogs; and other means of affecting meibomian gland secretions.

In another prior art reference, Textbook of Dermatology, 4th Edition, A. Rook et al editors, Vol. 2, p. 2152, there is a disclosure that Demodectic blepharitis may be treated with bathing with boric acid or with benzalkonium.

In the article by Browning et al mentioned above, on p. 155, there is a disclosure that for treatment of ocular rosacea only tetracycline has been critically studied. In the same article, there is mentioned that metronidazole has been used for treatment of skin lesions of rosacea. However, the article does not teach the use of a nitromidazole compound (including metronidazole) with a suitable carrier for topical treatment of ocular tissues.

In another reference, namely "Topical Metronidazole Therapy For Rosacea", by P. A. Bleicher et al, Arch Dermatol., Vol. 123, May 1987, pp. 609-614, there is a disclosure that metronidazole can be used in a gel for treatment of rosacea of the skin. However, there is no disclosure that metronidazole can be used for ocular rosacea.

The prior art also teaches other treatments for eye inflammations using the direct application of a treating composition to the eye. For example, in U.S. Pat. No. 4,612,193 to Gordon et al, there is a disclosure that a blepharitic infection (not characterized as being caused by ocular rosacea) can cause a stye and that an ointment is provided to treat the stye. The ointment is based on yellow mercuric oxide, boric acid, and wheat germ oil.

In the book Diseases of the Cornea, 2nd Edition, by M. G. Grayson, C. Z. Mosby Company, 1983, pp. 119-209, there is a disclosure that blepharitis can be treated using antibiotic ointments containing antibiotics such as bacitracin, erythromycin, chloramphenicol, and tetracycline. Other active agents for treating blepharitis include Rifampin, a very dilute steroid such as 0.12%, prednisolone, and polysulfide.

The prior art treatments for eye inflammations have several disadvantages. For example, when tetracycline is taken orally it takes between two to three months to have a significant effect. Furthermore, tetracycline is plagued with side effects such as super infections, light sensitivity, cramp feelings of the user, contra-indication if the user is pregnant, and resultant feelings that are similar to those when a person has the flu. Therefore, it would be desirable to avoid the use of tetracycline for the treatment of eye inflammations (e.g. ocular rosacea and related conditions).

Another eye condition is known as dry eye which results from an abnormal difficiency of tear production. A discussion of dry eye is found in the article entitled "Tear Physiology and Dry Eyes" by F. J. Holly et al, Survey of Ophthalmology, Vol. 22, No. 2, September-October 1977, pp. 69-87. As disclosed in the Holly et al article, the primary treatment for dry eye is the use of artificial tears applied topically. Unfortunately, blepharitis is often misdiagnosed as dry eye. As a result, treatment with artificial tears is inadequate to cure the patient's problem. It would be desirable to provide a pharmaceutical composition that would treat the actual blepharitis in the instance where the condition was misdiagnosed as dry eye.

Another problem that has received attention in the ophthalmological literature lately is infection by a parasite known as Acanthamoeba hystolytica which particularly plagues users of contact lenses. A particularly devastating infection results from this parasite leaving the victim particularly susceptible to blindness in an infected eye. A presently used treatment for Acanthamoeba is a therapeutic agent known as brolene which is an over-the-counter British stye medication. Other known treatments for Acanthamoeba include antibiotics such as micadasol and mediasforan. However, it would be desirable if another nonantibiotic agent could be applied topically to alleviate the deleterious conditions caused by the Acanthamoeban organism.

Another problem associated with wearers of contact lenses is the formation of lumps under the lenses. Lumpy deposits formed under the contact lenses are very often due to undiagnosed blepharitis. By alleviating the underlying blepharitis condition, the cause of lump formation under contact lenses could be alleviated or removed. In this respect, it would be desirable to provide a treatment to prevent lump formation under contact lenses that result from undiagnosed blepharitis.

Although systemic treatments for eye conditions are known, such treatments are not popular with ophthalmologists. An eye doctor generally prefers to prescribe an eye medicine that is administered topically to the eye rather than prescribe a pill or the like which administers the medicine systemically. Therefore, it would be desirable to provide a treatment for blepharitis, or blepharoconjunctivitis, or ocular rosacea generally that is administered in a form such as a topically applied ointment or topically applied drops.

SUMMARY OF THE INVENTION

Accordingly, it is an object of the present invention to alleviate the disadvantages and deficiencies of the prior art by providing a treatment for blepharitis, blepharoconjunctivitis, and ocular rosacea that is administered in the form of eye drops or other topically administered eye preparations.

Another object of the invention is to provide a treatment that avoids the use of tetracycline or other antibiotics for treating ocular inflammations such as ocular rosacea and related conditions.

Another object of the invention is to provide a pharmaceutical composition that treats actual blepharitis in an instance where the actual condition is misdiagnosed as dry eye.

Still another object of the invention is to provide a topical treatment for the eye conditions resulting from infection by Acanthamoeba hystolytica.

Yet another object of the invention is to provide a treatment to prevent lump formation under contact lenses that result from undiagnosed blepharitis.

In accordance with the teachings of the present invention, a pharmaceutical composition is provided for treating blepharitis and blepharoconjunctivitis generally and especially associated with ocular rosacea. The pharmaceutical composition of the invention includes an amount of a nitroimidazole compound effective for treating the blepharitis and/or blepharoconjunctivitis and/or ocular rosacea; and a carrier for the nitroimidazole compound wherein the carrier is suitable for direct application to the eye tissues. The nitroimidazole compound is selected from the group consisting of metronidazole, nimorazole, tinidazole, ordinidazole, secnidazole, and carnidazole. The preferred compound is metronidazole.

The carrier may be in the form of an ointment, e.g. petrolatum-based or a water soluble gel, or in the form of a liquid to be applied to the eye in the form of eye drops.

The preferred carrier for eye drops is an artificial tear composition including primarily isotonic sodium chloride. In addition, a cellulose ether such as methylcellulose may be added to the artificial tear carrier. Other cellulose ethers such as hydroxypropylmethylcellulose and hydroxyethylcellulose may be included in the artificial tear carrier. The artificial tear composition may also include a polyvinyl alcohol.

The composition of the invention is applied to ocular tissues directly for treating the conditions of blepharitis, blepharoconjunctivitis, and ocular rosacea.

These and other objects and advantages of the present invention will become apparent from a reading of the following specification.

DESCRIPTION OF THE PREFERRED EMBODIMENT

Here are represented several formulations for pharmaceutical compositions of the invention.

EXAMPLE 1

One gram of metronidazole is added to 1,000 grams of artificial tear carrier with stirring. The artificial tear carrier is isotonic sodium chloride solution. This formulation provides an approximately 0.1% solution of metronidazole in artificial tear carrier for application to the patient by means of eye drops.

EXAMPLE 2

7.5 grams of metronidazole are added to 992.5 grams of artificial tear solution with stirring to provide a formulation containing approximately 0.75% metronidazole in an artificial tear carrier.

EXAMPLE 3

10 grams of metronidazole are added to 990.0 grams of isotonic sodium chloride solution with stirring to provide a 1% metronidazole solution in isotonic sodium chloride carrier.

EXAMPLE 4

An eye drop formulation is made up by blending the following: 10 grams metronidazole, 10 grams methylcellulose, and 980 grams isotonic sodium chloride. This formulation contains approximately 1% metronidazole, 1% methylcellulose, and the balance being isotonic sodium chloride carrier.

EXAMPLE 5

Another eye drop formulation is made up by blending the following: 10 grams metronidazole, 14 grams polyvinyl alcohol, and 976 grams isotonic sodium chloride artificial tear solution. The resulting formulation contains approximately 1% metronidazole, 1.4% polyvinyl alcohol, and the balance being artificial tear carrier.

EXAMPLE 6

Another eye drop formulation is made by blending the following: 15 grams metronidazole and 985 grams of isotonic sodium chloride artificial tear solution with stirring to provide a 1.5% metronidazole solution.

EXAMPLE 7

Another eye drop formulation is made by stirring 20 grams metronidazole into 980 grams of artificial tear solution to provide a 2.0% metronidazole solution.

EXAMPLE 8

The following ointment can be prepared by blending 10 grams of metronidazole thoroughly with 990 grams petrolatum vehicle (an ointment base) to provide an ointment suitable for application to the ocular tissues which contains 1% metronidazole.

EXAMPLE 9

The following ointment can be prepared by blending 15 grams of metronidazole thoroughly with 985 grams petrolatum vehicle (an ointment base) to provide an ointment suitable for application to the ocular tissues which contain 1.5% metronidazole.

EXAMPLE 10

The following ointment can be prepared by blending 20 grams of metronidazole thoroughly with 980 grams petrolatum vehicle (an ointment base) to provide an ointment suitable for application to the ocular tissues which contains 2% metronidazole.

By employing the principles of the invention, numerous objects are realized and numerous benefits are obtained. For example, a pharmaceutical composition is provided to treat blepharitis, blepharcoconjunctivitis, and ocular rosacea and is administered in the form of an ointment or in the form of eye drops. The method of treatment of the invention avoids the use of tetracycline for treating ocular rosacea and related conditions. With the invention, a pharmaceutical composition is provided that treats actual blepharitis in the case where the condition is misdiaqnosed as dry eye. The invention provides a topical treatment for eye conditions resulting from infection by Acanthamoeba hystolytica. The invention provides a treatment to prevent lump formation under contact lenses that result from blepharitis.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A pharmaceutical composition, comprising:
    an amount of metronidazole effective to treat blepharitis and blepharoconjunctivitis in an animal or human patient; and
    a carrier for said metronidazole compound, said carrier suitable for topical application to ocular tissues, wherein said carrier includes an artificial tear composition.

2. The pharmaceutical composition described in claim 1 wherein said artificial tear composition includes isotonic sodium chloride.

3. The pharmaceutical composition described in claim 2 wherein said artificial tear composition includes a cellulose derivative.

4. The pharmaceutical composition described in claim 3 wherein said cellulose derivative is a cellulose ether.

5. The pharmaceutical composition described in claim 4, wherein said cellulose ether is present as approximately 1% by weight of said artificial tear carrier.

6. The pharmaceutical composition described in claim 3 wherein said cellulose derivative is selected from the group of cellulose ethers consisting of methylcellulose, hydroxypropylmethylcellulose, and hydroxyethylcellulose.

7. The pharmaceutical composition described in claim 6 wherein said cellulose derivative includes methylcellulose.

8. The pharmaceutical composition described in claim 2 wherein artificial tear composition includes polyvinyl alcohol.

9. The pharmaceutical composition described in claim 8 wherein said polyvinyl alcohol is present as approximately 1.4% by weight of said artificial tear carrier.

10. A method of treating a human being for blepharitis or blepharoconjunctivitis, which comprises: administering to said human being an amount of metronidazole applied directly to ocular tissues effective to treat the blepharitis or blepharoconjunctivitis.

11. A method of treating a human being for blepharitis or blepharoconjunctivitis which comprises: administering to said human being an amount of a compound in the class of nitroimidazole compounds applied directly to ocular tissues effective to treat the blepharitis or blepharoconjunctivitis.

12. The method of treating blepharitis or blepharoconjunctivitis described in claim 11 wherein the nitroimidazole compound is selected from the group consisting of metronidazole, nimorazole, tinidazole, ordinidazole, secnidazole, and carnidazole.

13. The method of treating blepharitis or blepharoconjunctivitis described in claim 12 wherein the nitroimidazole compound is metronidazole in a range of 0.1–2% by weight.

* * * * *